United States Patent [19]
Horwitt

[11] 4,283,703
[45] Aug. 11, 1981

[54] VIBRATION-RESISTANT PROBE-LIKE ELECTRICAL HEATERS

[75] Inventor: Laurence G. Horwitt, New Haven, Conn.

[73] Assignee: Sun Chemical Corporation, New York, N.Y.

[21] Appl. No.: 71,753

[22] Filed: Aug. 31, 1979

[51] Int. Cl.³ .................. H01L 7/00; H05B 3/08; G01N 27/26
[52] U.S. Cl. .................. 338/34; 204/195 S; 219/541; 219/546; 338/268; 338/270; 338/271; 338/302
[58] Field of Search .................. 204/195 S; 219/205–208, 227, 236, 237, 270, 335, 336, 523, 534, 541, 546; 338/28, 30, 34, 270, 271, 268, 273, 302–303, 326

[56] References Cited

U.S. PATENT DOCUMENTS

| 2,484,544 | 10/1949 | Bennett et al. | 219/270 |
| 2,485,496 | 10/1949 | Korsgren et al. | 338/271 X |
| 3,498,279 | 3/1970 | Seeley, Jr. | 219/207 X |
| 4,155,827 | 5/1979 | Maurer et al. | 204/195 S |
| 4,169,778 | 10/1979 | Mann et al. | 204/195 S |
| 4,175,019 | 11/1979 | Murphy | 204/195 S |

Primary Examiner—Donald R. Valentine
Attorney, Agent, or Firm—Cynthia Berlow

[57] ABSTRACT

A probe-like, vibration-resistant fast-heating electrical heater assembly for use in a pollution sensor of an exhaust monitoring system for internal combustion engines, which comprises an elongate metal tube having concentrically disposed therein a metal conductor rod which is insulated from the tube. At one pair of corresponding ends, the tube and rod carry a ceramic coil form having an open winding on it comprising a helical resistance coil that is disposed in a helical groove of the coil form. Ceramic cement is utilized to secure the coil form in place, and also to mount the conductor rod in the conductor tube whereby a rigid, vibration-resistant assemblage is had that can also withstand high temperatures. The conductor tube is carried in a terminal post that has an annular flange at one end for the purpose of mounting the heater assembly in the associated equipment.

3 Claims, 12 Drawing Figures

U.S. Patent    Aug. 11, 1981    Sheet 1 of 2    4,283,703
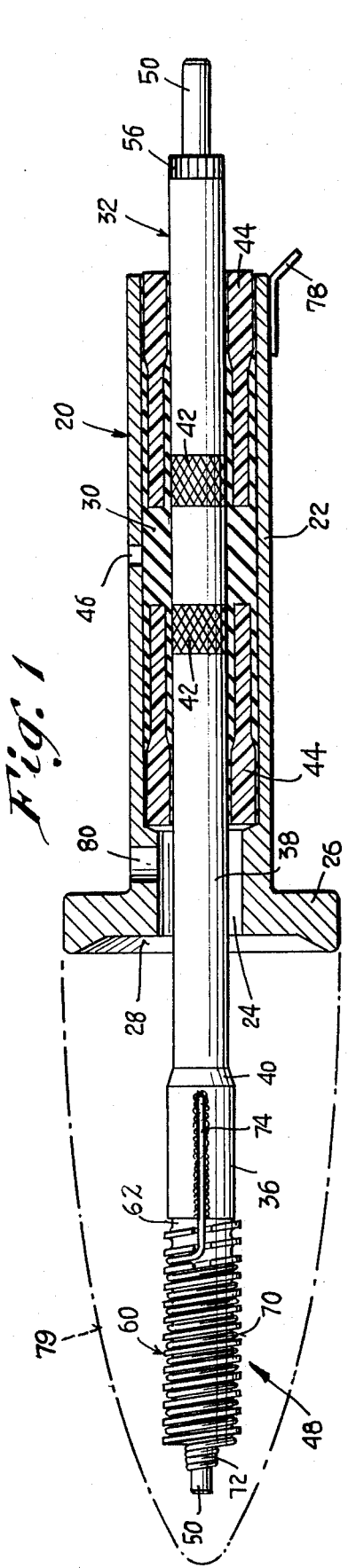
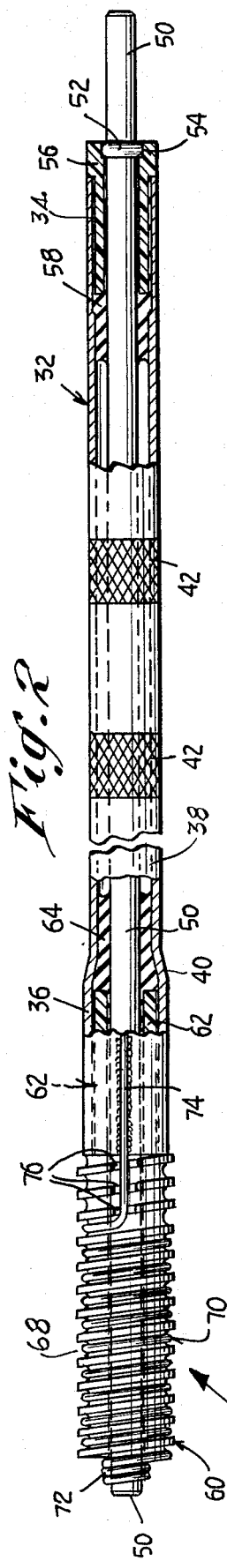
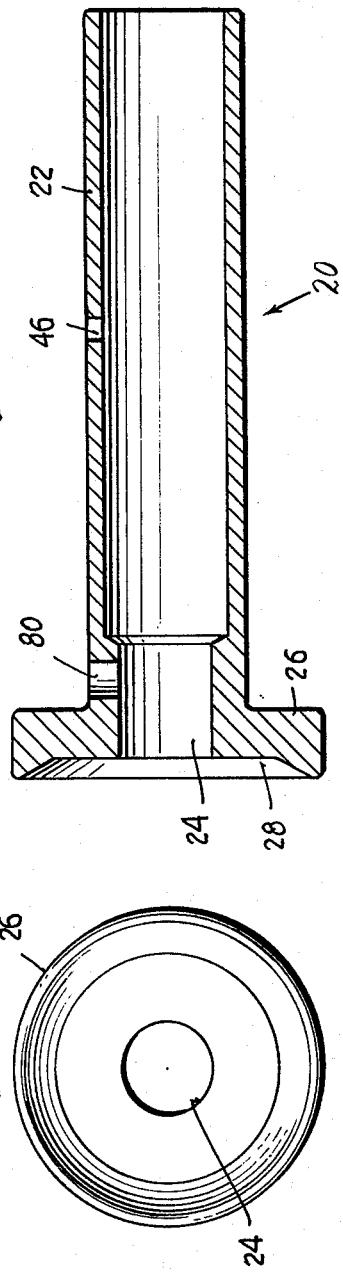

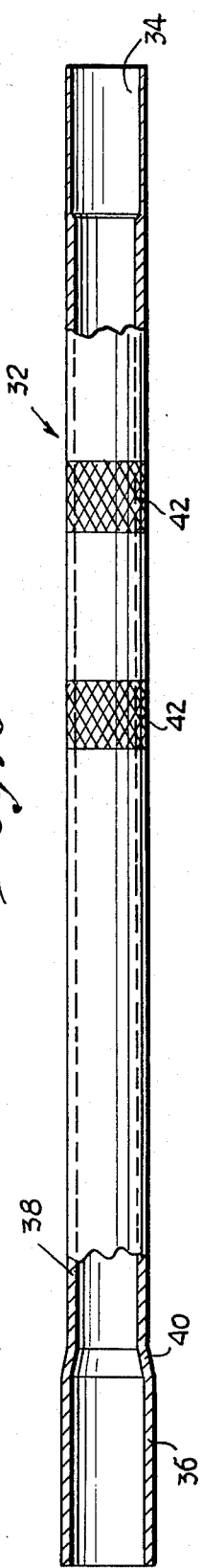
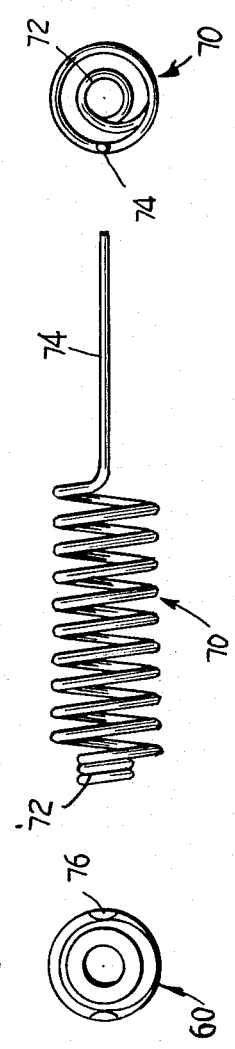
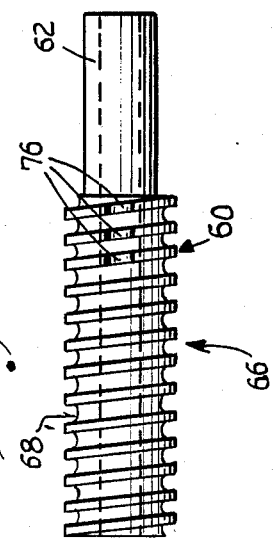
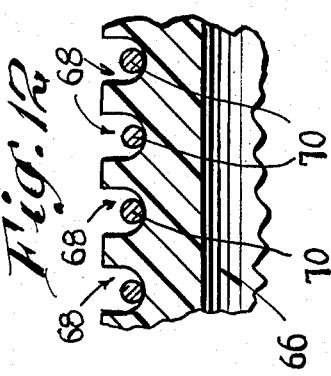
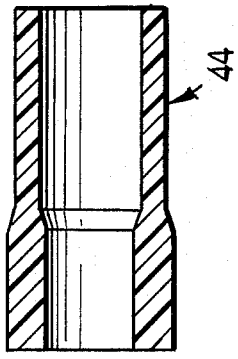

VIBRATION-RESISTANT PROBE-LIKE ELECTRICAL HEATERS

BACKGROUND

This invention relates to probe-like electrical heater devices, and more particularly to such devices which are intended for use in pollution control systems, such as those employing zirconia oxygen sensors or titanium dioxide sensors as used with internal combustion engines where the environment involves relatively strong, vibratory forces which are likely to be generated by the engines.

In the past, probe-like electrical heater devices have been utilized in various situations, to bring concentrated heat to a small area. One well-known use of such heater devices is in electrical cigar lighters, where a plug-like ignitor unit has at its inner end a spiral heating coil that is arranged to contact and ignite the end of a cigar or cigarette. Although a certain amount of vibration was involved in such use, the disruptive forces were usually not sufficiently severe to warrant extreme measures to combat them.

In a somewhat lesser degree, the same is true of ignitor or glow plugs as utilized in the combustion chambers of diesel engines and the like.

With the advent of increased automobile use and a greater awareness of environmental pollution, new control devices are being considered to monitor the exhaust gases of internal combustion engines. One such device is the zirconia oxygen sensor, and another is the titanium dioxide sensor, both of which involve a probe-like electrical heating coil assemblage that is subjected to the flow of oxygen and/or other gases. Sensors such as these are associated with automobile exhaust systems, where strong vibrations are likely to occur. Previously produced probe-like electrical heaters as tested in this environment have not had a satisfactory, useful life. The continuous heating of the resistance coil in its electrically energized condition has contributed to coil failures while other components of the devices remained operative. Also, prior devices were found to be too slow in heating.

SUMMARY

The above drawbacks and disadvantages of prior probe-like electrical heating devices are obviated by the present invention, which has for one object the provision of a novel and improved probe-like electrical heater which can withstand considerable vibration forces without the likelihood of failure or short circuit, especially of the heater coil.

Another object of the invention is to provide an improved probe-like electrical heater as above set forth, which is especially simple in its construction, being constituted of relatively few parts that can be readily manufactured and assembled.

A further object of the invention is to provide an improved, probe-like electrical heater in accordance with the foregoing, which is relatively inexpensive to manufacture and which readily lends itself to mass production techniques.

Yet another object of the invention is to provide an improved, probe-like electrical heater as above characterized, which is effective and reliable in its functioning, and which efficiently produces the necessary heating at the desired location.

A still further object of the invention is to provide an improved, probe-like electrical heater as outlined, which has an especially short or quick heating time.

A feature of the invention resides in the provision of an improved, probe-like electrical heater assemblage of the type described, which can withstand especially high temperatures without malfunction or failure.

Still other objects and advantages will hereinafter appear.

In accomplishing the above objects the invention provides, in the illustrated embodiments thereof a probe-like electrical heater assembly having an elongate metal tube which is adapted to constitute a coil support and also to carry an electrical current. Extending through, and insulated and spaced from the support tube is a metal conductor rod. At corresponding ends of the tube and rod there is mounted a ceramic coil form which has a hub that is fitted and cemented into the tube. The coil form has a helical exterior groove, in which there is disposed a helically-wound electrical resistance coil that occupies a relatively small area of the groove. Cylindrical ceramic insulators are utilized to position the conductor rod in the metal tube, and also to position the metal tube in a terminal post that has means for mounting the assemblage on associated equipment. One pair of corresponding ends of the conductor tube and rod are arranged to be accommodated in an electrical connector member for the purpose of bringing current to the heating coil.

In the accompanying drawings:

FIG. 1 is an axial sectional view of the electrical probe-like heater device of the invention, with some portions thereof being shown in side elevation.

FIG. 2 is a view partly in axial section and partly in side elevation, of the electrical heater assemblage of the device shown on a slightly enlarged scale.

FIG. 3 is an axial sectional view of the tubular terminal post of the heater device.

FIG. 4 is an elevational view of the left end of the terminal post of FIG. 3.

FIG. 5 is a view partly in axial section and partly in side elevation, of the conductor tube component of the heater device.

FIG. 6 is a side elevational view of the ceramic coil insulator component of the heater device.

FIG. 7 is an end elevational view of the ceramic coil insulator component.

FIG. 8 is a side elevational view of the helical resistance-coil of the heater device.

FIG. 9 is an end elevational view of the resistance coil of FIG. 8.

FIG. 10 is an axial sectional view of one of the terminal post insulators of the electrical heater device, FIG. 11 is an axial sectional view of a conductor rod insulator of the heater device, and FIG. 12 is a fragmentary axial section through the heating coil and its ceramic support or coil insulator.

Referring first to FIGS. 1 and 3, the vibration-resistant electrical heater device or assembly of the present invention comprises a tubular terminal post component 20 which can be constituted of stainless steel. The terminal post 20 has a cylindrical body portion 22 having, at one end, a bore 24 of reduced diameter and a mounting structure in the form of an annular external mounting flange 26 provided with a dished, end face or surface 28.

Carried in and securely affixed to the terminal post 20 by means of ceramic cement 30 is an elongate probe-like heater assemblage comprising a conductor tube 32 which can be advantageously formed of stainless steel, said tube having at one end a bore 34 enlarged diameter, formed for example by reaming out the end of the tube for a predetermined distance as indicated.

At its other end, the conductor tube 32 is expanded in diameter, providing an end portion 36 of cylindrical configuration with an enlarged diameter, which joins the main body part 38 of the tube at a shoulder formation 40.

Intermediate its ends, the conductor tube 32 is provided with a series of diamond knurls 42 for the purpose of effecting a secure retention of the conductor tube in the terminal post 20, by engagement of the knurls with the ceramic cement 30.

Initial positioning of the conductor tube 32 in the terminal post 20 is effected by a pair of tubular, terminal-post insulators 44 constituted of ceramic material, see FIGS. 1 and 10.

Intermediate its ends the terminal post 20 has an opening 46 in its wall, through which the cement 30 is introduced in liquid or pasty form, such cement filling all of the voids or spaces that exist inside of the terminal post, between the latter, the tubular insulators 44 and the conductor tube 32. When the cement 30 has set, the conductor tube 32 will be securely affixed in the terminal post 20, as can now be readily understood.

The heater assembly, designated generally by the numeral 48 in FIG. 1, further comprises a centrally disposed conductor rod 50 having an annular shoulder 52 adjacent one end which fits into an annular recess 54 of a tubular conductor-rod insulator 56 that is preferably constituted of ceramic material. The insulator 56 is received in the enlarged bore 34 of the conductor tube 32 and is cemented in place by cement 58 as shown in FIG. 2.

At its other enlarged end 36 the conductor tube 32 mounts an electrical heater unit comprising a ceramic coil insulator 60 having a smooth shank-mounting portion 62 which is received in the enlarged end 36 of the conductor tube and is secured in place by ceramic cement 64. The coil insulator 60 has a body portion 66 characterized by an exterior helical groove 68 which is arranged to accommodate a helically-coiled, electrical-resistance unit 70 as shown in FIGS. 1, 2 and 8. The resistance unit or coil 70 has at one end a tightly-coiled portion 72 of reduced diameter which snugly fits the associated end of the conductor rod 50 and is welded thereto. The other end of the electrical coil 70 has a straight terminal portion 74 which overlies the enlarged end 36 of the conductor tube 32 and is welded thereto as indicated in FIG. 1. The helical portion of the electrical coil 70 is tightly accommodated in the helical groove 68 of the ceramic coil insulator 60 as shown, whereby it is not readily dislodged thereform in spite of being subjected to severe vibration forces. As seen in FIG. 12, the wire of the coil 70 occupies relatively little space in the helical groove, and has only a limited area of contact whereby the coil form 60 does not act to conduct as much heat from the wire as it would if a large area of contact existed due to the groove diameter closely approximating the coil diameter. Thus, a much faster heating of the coil 70 occurs, making for a very quick response or heating time. The wire diameter of the coil 70 is only a small fractional part of the diameter of the groove 68 of the coil form 60. Crest portions of the insulator body 66 have aligned notches 76 which provide clearance for the straight terminal portion 74 of the coil, as seen in FIGS. 1 and 2.

A wire lead 78 can be welded to one end of the terminal post 20 as indicated in FIG. 1, to provide a reliable ground connection to the post. The projecting ends of the conductor rod 50 and conductor tube 32 are adapted to be received in a suitable electrical connector socket, as will be readily understood.

By virtue of the construction provided, the conductor tube 32 is electrically insulated from the terminal post 20, whereby the latter can be grounded by means of the wire 78 without interference with the circuitry of the associated equipment.

The electrical heater device of the invention is intended for use with equipment having, for example, a ceramic cone 79 arranged to encompass the heating coil 70 as indicated by the broken outline in FIG. 1. The terminal post 20 has an opening 80 in its side wall adjacent the mounting flange 26, for the introduction of oxygen which will flow to the interior of the ceramic cone 79 and surround the electrical heating coil 70. The gas entering the opening 80 is utilized in the determination of the pollution content of the exhaust gases, in a zirconia oxygen or other sensor device intended to be connected with the exhaust system of the internal combustion engine.

It will now be seen from the foregoing that I have provided an improved probe-like, vibration-resistant electrical heater assembly for use with pollution control equipment, which assembly is relatively simple and inexpensive to produce while at the same time being extremely rugged and resistant to vibration forces. The assembly, being constituted of high-temperature components formed of stainless steel, ceramic cement etc. will resist the action of high temperatures, an has been found to function reliably for the intended purpose even under adverse conditions including strong vibratory forces. The resistance coil 70 heats very quickly yet it is not readily dislodged, remaining at all times securely connected in the circuit by virtue of its ends being welded respectively to the conductor rod 50 and conductor tube 36.

It can be seen from an inspection of FIG. 12 that the wire of the coil 70 is deeply received in the helical groove 68, resulting in a sturdy, vibration-resistant unit. The slight expansion of the wire when it is heated is not enough to appreciably affect its deep seating, and the usual weakening of the wire due to its heating is also insufficient to enable dislodgement from the coil form 66. Thus, the construction provided by the invention is characterized by a long, reliably useful life cycle.

Variations and modifications are possible without departing from the spirit of the claims.

I claim:

1. A probe-like vibration-resistant electrical heater assembly for use in an oxygen sensor of an exhaust monitoring system for internal combustion engines, comprising in combination:
    (a) an elongate metal tube adapted to constitute a support and to carry an electrical current, one end portion of said tube being of enlarged diameter,
    (b) an elongate metal conductor member extending through and spaced from said support tube, said conductor member projecting from said one enlarged-diameter end portion of the tube and forming therewith an annular space at said end portion,
    (c) a tubular ceramic coil form surrounding and carried on the projecting end of the metal conductor member, (d) said coil form having a hub disposed and closely fitting into the said annular space at the enlarged-diameter end portion of the tube,
(e) said coil form having a helical groove in its exterior surface, and
(f) a helical heating coil of wire disposed in the helical groove of the coil form and having its ends secured to an exterior surface of the metal tube and to the metal conductor member so as to enable the coil to be energized,
(g) said hub, conductor member and enlarged-diameter end portion of said tube constituting a rigid, unitary direct-engaging assemblage, and said hub having a loose-fit in and being cemented in said enlarged-diameter portion of the tube.

2. An electrical heater assembly as in claim 1, wherein:
(a) said coil form has, at one end of its helical groove, an axially-extending slot in which an end portion of the heating coil is disposed.

3. The invention as defined in claim 1, wherein:
(a) the hub of the ceramic coil form has a loose fit on the conductor member and is cemented thereto.

* * * * *